United States Patent [19]

Cummins

[11] 4,388,327

[45] Jun. 14, 1983

[54] METHOD OF INCREASING MILK PRODUCTION OF DAIRY CATTLE

[75] Inventor: Earl W. Cummins, Wilmington, Del.

[73] Assignee: E. I. Du Pont de Nemours & Co., Wilmington, Del.

[21] Appl. No.: 316,935

[22] Filed: Oct. 30, 1981

[51] Int. Cl.$^3$ .............................................. A23L 1/30
[52] U.S. Cl. ....................................... 426/2; 426/648; 426/656; 426/807
[58] Field of Search ................... 426/2, 648, 807, 656; 562/581; 424/317

[56] References Cited

U.S. PATENT DOCUMENTS

| | | |
|---|---|---|
| 3,272,866 | 9/1966 | Nufer . |
| 3,761,518 | 9/1973 | Haglid ................................. 426/648 |
| 3,773,927 | 11/1973 | Cummins ............................ 424/317 |
| 4,175,121 | 11/1979 | Mantha ................................. 424/94 |

OTHER PUBLICATIONS

"The Effect of DuPont Hydan ® Feed Supplement on Fat-Corrected Milk Production of Dairy Cows", DuPont Brochure E–43604.
"Hydan ®, Hydan ® L Feed Supplements" DuPont Brochure E–43619, 10/81.
"Information Bulletin Hydan ® L" DuPont Brochure E–43622, 10/81.
*Journal Dairy Science*, vol. 51, No. 11, pp. 1866–1868.
*Feedstuffs*, vol. 43, No. 5, p. 31.

*Primary Examiner*—William F. Smith

[57] ABSTRACT

The weight of milk produced by dairy cattle can be increased by supplementing the diets of the cattle with γ-methylmercapto-α-hydroxybutyric acid and its oligomers.

3 Claims, 1 Drawing Figure

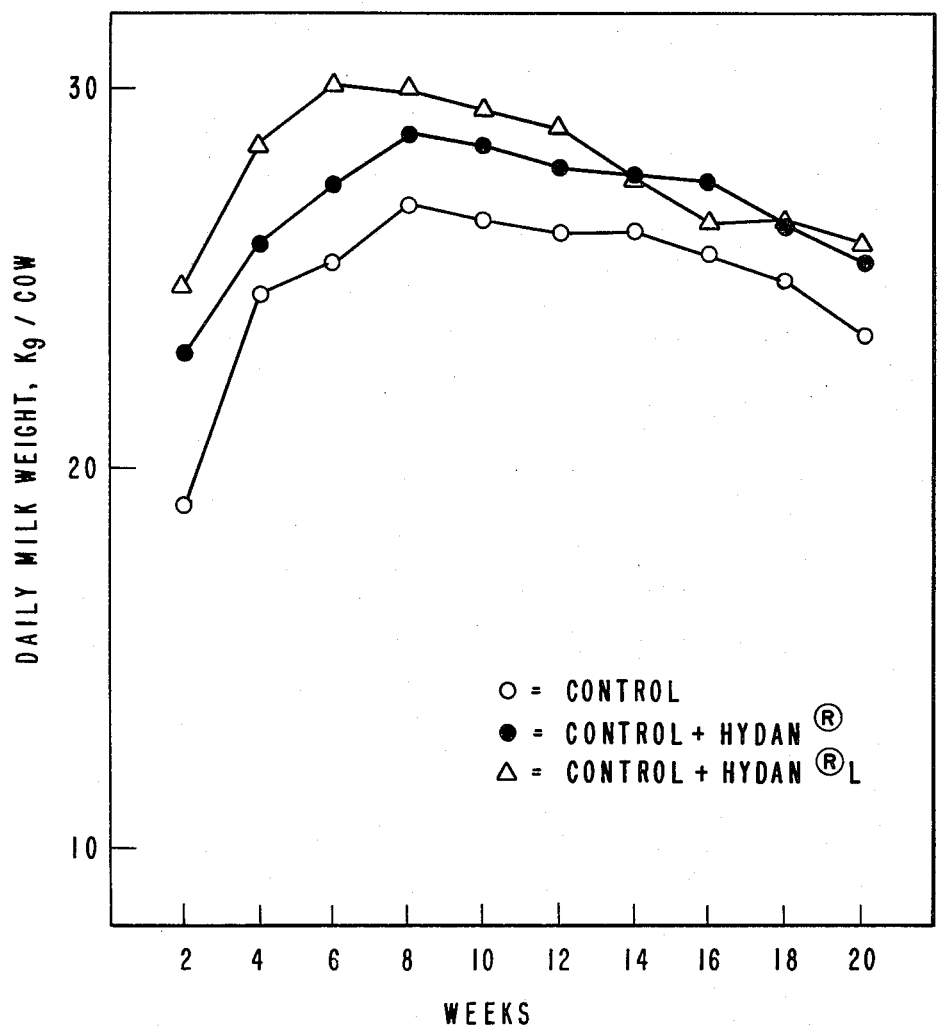

METHOD OF INCREASING MILK PRODUCTION OF DAIRY CATTLE

BACKGROUND OF THE INVENTION

This invention relates to a method for increasing the milk production from dairy cattle.

The hydroxy analog of methionine, γ-methylmercapto-α-hydroxybutyric acid (hereinafter referred to as "free acid") has nutrient values equivalent to the corresponding amino acid, methionine. The hemicalcium salt of γ-methylmercapto-α-hydroxybutyric acid (hereinafter referred to as the "calcium salt") has been used to fortify various animal feeds for years.

It is known that the milk production of dairy cattle can be increased by supplementing the diets of the cattle with the calcium salt. See, for example, L. C. Griel, Jr., et al., "Milk Production Response to Feeding Methionine Hydroxy Analog to Lactating Dairy Cows", *Journal of Dairy Science*, Vol. 51, No. 11, pages 1866–1868, and Bishop, "Methionine Hydroxy Analog Supplementation in Beef and Dairy Cattle," *Feedstuffs*, Vol. 43, No. 5, p. 31. U.S. Pat. No. 4,175,121 to Mantha, dated Nov. 20, 1979, discloses a calcium salt containing feed supplement also containing a fermentation enzyme extract which, when fed to dairy cattle in effective amounts, can increase milk production. In all of this work, it is the calcium salt which is fed to the cows, not the free acid. Applicant is not aware of any reference in the art to the use of the free acid as a feed supplement for dairy cattle.

SUMMARY OF THE INVENTION

It has now unexpectedly been found that the use of a product containing free acid and its oligomers as a feed supplement for dairy cattle is more effective than the use of the calcium salt in increasing the milk production of dairy cattle. This invention therefore relates to a method of increasing the milk production from dairy cows comprising feeding to said cows as part of their diet a feed supplement consisting essentially of an effective amount of a product containing free acid and about 10 to 75%, based on total equivalent free acid, of oligomers of free acid.

DETAILED DESCRIPTION OF THE INVENTION

The free-acid, γ-methylmercapto-α-hydroxybutyric acid, can be represented by the following chemical formula:

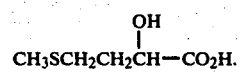

One of the characteristics of this molecule is that it will equilibrate according to the following equation; where R=CH$_3$SCH$_2$CH$_2$—:

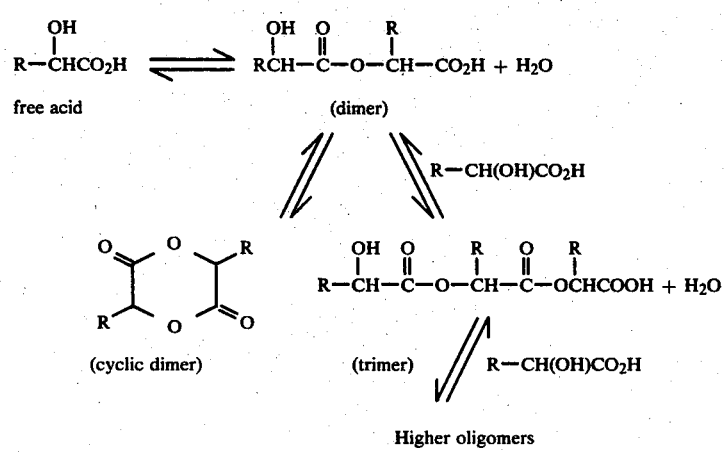

All of the above combined forms of free acid and their combinations are referred to collectively as "oligomers".

The feed supplement used in this invention can be prepared according to U.S. Pat. No. 3,773,927 to Cummins, dated Nov. 20, 1973. This patent describes the preparation of free acid by hydrolyzing γ-methylmercapto-α-hydroxybutyronitrile with hydrochloric acid. A product produced in this manner contains about 40% free acid by weight along with small amounts of oligomers. A product with higher oligomer content can be obtained by removal of water by distillation, preferably at about 100° to 125° C. The more water removed, the higher the oligomer content of the prouct.

It is preferred that the oligomer content of the feed supplement used in the method of this invention be within the range of about 10 to 75% based on total equivalent free acid. More preferably, the oligomer content will be from about 20 to 60%.

The optimum intake of the feed supplement of this invention will vary with the breed of cow and the stage of the cow's milk-producing cycle. In general, a daily intake of approximately 20 to 40 grams of the supplement per cow should be effective in increasing milk production. The supplement can be added to a typical dairy feed (e.g., one composed of ground grains such as corn, oats, wheat, soybeans, etc.) to provide approximately two to five pounds of the supplement per ton of dry matter.

The following examples illustrate the preparation of the free acid used in this invention and its utility in increasing the volume of milk produced by dairy cattle.

EXAMPLE 1

A reactor was charged with 514 parts of 31.2% hydrochloric acid. To this was added 524.4 parts of γ-methylmercapto-α-hydroxybutyronitrile over a 14-minute period. After the addition was 50% complete, the temperature of the mixture had reached 90° C. The temperature was maintained below 95° C. during the remainder of the addition by means of external cooling with an ice-bath. The resulting slurry was heated with steam for an additional 90 minutes.

The reaction mass was then concentrated during 5 hours at 80 torr until the pot temperature reached 100° C.

The resulting residue was cooled to 30° C. and filtered. The liquid was analyzed by HPLC and found to contain 48% free acid. When 25 parts of the liquid was hydrolyzed for two hours at 98° C. with 97.5 parts of 1 N hydrochloric acid (to convert the oligomers to free acid) and reanalyzed, it was found to contain 92.5% free acid equivalent. This corresponds to an oligomer content at 48.1%, calculated as follows.

$$\% \text{ oligomer} = \left( \frac{M_s - M}{M_s} \right) \times 100\%$$

where $M_s = \%$ free acid after hydrolysis with 1 N hydrochloric acid, i.e., free acid equivalent.

$M = \%$ free acid before hydrolysis with 1 N hydrochloric acid.

EXAMPLE 2

Twenty-four Holstein cows were used to form three groups equalized for age, date of calving and previous production records. Groups were randomly assigned to three treatments: (1) control, (2) control plus Hydan ® (trademark of calcium salt of γ-hydroxy-α-methylmercaptobutyric acid, E. I. du Pont de Nemours and Co., Wilmington, Del.) at 0.15% of total ration dry matter, and (3) control plus Hydan ®L (trademark for γ-hydroxy-α-methylmercaptobutyric acid, and its oligomers, E. I. du Pont de Nemours and Co., Wilmington, Del.) at 0.136% of ration dry matter. The Hydan ® and Hydan ®L contents of treatments (2) and (3) respectively were calculated so as to provide a molecular equivalent amount of calcium salt and free acid equivalent in each treatment. Each cow received treatment ration from two weeks prior to scheduled date of calving and for 112 days of production. All cows received control ration for 28 days post-treatment. Experimental measurements were taken daily and condensed into ten consecutive biweekly averages.

The composition of the three rations is shown in Table 1. Hydan ® (93% calcium salt) was premixed with soybean meal at the rate of 30 g per kg. Hydan ®L (90.4% free acid equivalent, containing 23% oligomer) was premixed with soybean meal at the rate of 27.2 g per kg. All ration components were mixed together and fed as a complete mixed ration to insure uniform intake of component proportions.

Treatment means adjusted for differences in average body weight are shown in Table 2 across all ten biweekly periods. There were no significant differences due to treatment. Dry matter intake and daily milk production tended to be significantly higher with the Hydan ® compounds as compared to control. This tendency was more pronounced with Hydan ®L than with Hydan ®.

The FIGURE graphically displays least-square treatment means by 14-day intervals for the measurements associated with milk production. Significant pairwise differences within periods are shown at the bottom of each figure by the symbol +. Rations are designated 1, 2 or 3 for control, Hydan ® and Hydan ®L, respectively. The symbol + in the column below week 4 and in the row designated 3>2 indicates, for example, that in week 4, the daily milk weight of cows receiving control plus Hydan ®L was significantly greater than that of cows receiving control plus Hydan ®. Milk weight during weeks 4 and 6 was significantly higher with Hydan ®L than with Hydan ®.

No unusual change in performance during weeks 18 and 20 due to removal of Hydan ® and Hydan ®L from rations after week 16 was observed.

TABLE I

| Ration Dry Matter Composition | | | |
|---|---|---|---|
| | Ration % by Weight | | |
| | Control | Hydan ® | Hydan ® L |
| Corn silage | 40.000 | 40.000 | 40.000 |
| Concentrate | 55.000 | 55.000 | 55.000 |
| Soybean meal | 5.000 | 4.850 | 4.864 |
| Hydan ® or Hydan ® L | — | .150 | .136 |
| Total | 100.000 | 100.000 | 100.000 |

TABLE II

| Least Squares Treatment Means | | | |
|---|---|---|---|
| | Treatment | | |
| | Control | Hydan ® | Hydan ® L |
| Body weight, kg.[a] | 585. | 579. | 577. |
| Dry matter, kg./day | 16.33 | 16.57 | 18.60 |
| Milk, kg./day | 24.96 | 26.86 | 27.90 |

[a] Unadjusted

What is claimed is:

1. A method of improving the milk production of dairy cows which comprises feeding to said cows as part of their diet a feed supplement containing an amount effective to improve milk production of γ-methylmercapto-α-hydroxybutyric acid and its oligomers, which oligomers are about 10 to 75% of the total equivalent free γ-methylmercapto-α-hydroxybutyric acid in said amount of the acid and its oligomers.

2. The method of claim 1 where the oligomers are about 20 to 60% of the total equivalent free -methylmercapto-α-hydroxybutyric acid in said amount of the acid and its oligomers.

3. The method of either claims 1 or 2 where the effective amount of γ-methylmercapto-α-hydroxybutyric acid as free acid equivalent is about 20 to 40 grams per day per cow.

* * * * *